United States Patent [19]

Scholl et al.

[11] Patent Number: 4,490,551
[45] Date of Patent: Dec. 25, 1984

[54] PROCESS FOR THE PRODUCTION OF URETHANES

[75] Inventors: Hans-Joachim Scholl, Koeln; Armin Zenner, Dormagen, both of Fed. Rep. of Germany

[73] Assignee: Bayer Aktiengesellschaft, Bayerwerk, Fed. Rep. of Germany

[21] Appl. No.: 125,008

[22] Filed: Feb. 27, 1980

[30] Foreign Application Priority Data

Mar. 2, 1979 [DE] Fed. Rep. of Germany ....... 2908250

[51] Int. Cl.³ ............... C07C 125/065; C07C 125/073
[52] U.S. Cl. .................................. 560/025; 560/024; 560/027; 560/028; 560/030; 560/032
[58] Field of Search ...................... 560/24, 25, 27, 28, 560/30

[56] References Cited

U.S. PATENT DOCUMENTS

| | | | |
|---|---|---|---|
| 3,338,956 | 8/1967 | Mountfield | 560/24 |
| 3,448,140 | 6/1969 | Gamlen et al. | 560/24 |
| 3,454,620 | 7/1969 | Gamlen et al. | 560/24 |
| 3,467,694 | 9/1969 | Hardy et al. | 560/25 |
| 3,531,512 | 9/1970 | Hardy et al. | 560/25 |
| 3,895,054 | 7/1975 | Zajacek et al. | 560/25 |
| 3,956,360 | 5/1976 | Zajacek et al. | |
| 3,993,685 | 11/1976 | Zaiacek et al. | 560/24 |
| 4,052,420 | 10/1977 | Licke | 560/25 X |
| 4,052,437 | 10/1977 | Licke | 560/25 |
| 4,080,365 | 3/1978 | Hirai et al. | 560/25 |
| 4,178,455 | 12/1979 | Hirai et al. | 560/24 |
| 4,230,876 | 10/1980 | Scholl et al. | 560/24 |

FOREIGN PATENT DOCUMENTS

| | | |
|---|---|---|
| 1080094 | 8/1967 | United Kingdom . |
| 1087896 | 10/1967 | United Kingdom . |
| 1246217 | 9/1971 | United Kingdom . |
| 1469222 | 4/1977 | United Kingdom . |
| 1472243 | 5/1977 | United Kingdom . |
| 1485108 | 9/1977 | United Kingdom . |
| 1486399 | 9/1977 | United Kingdom . |

OTHER PUBLICATIONS

Kondo et al., Chemistry Letters, Chemical Society of Japan, pp. 373–374, 1972.
Katsuharu et al., European Patent Application, publication number 0,000,815, 2/21/1979.

Primary Examiner—Bernard Helfin
Attorney, Agent, or Firm—Gene Harsh; Joseph C. Gil; Lyndanne M. Whalen

[57] ABSTRACT

A process for producing urethanes by reacting aromatic amino compounds with aliphatic, cycloaliphatic or araliphatic alcohols and carbon monoxide under conditions of elevated temperature and pressure characterized in that the reaction takes place in the presence of
(a) selenium, selenium compounds, sulfur and/or sulfur compounds,
(b) aromatic nitro compounds,
(c) tertiary organic amines and/or alkali metal salts of weak acids,
(d) oxidizing agents of a specified group and, optionally
(e) ammonia and/or aliphatic, araliphatic, cycloaliphatic or heterocyclic amines containing at least one hydrogen atom bound to an amine nitrogen.

24 Claims, No Drawings

PROCESS FOR THE PRODUCTION OF URETHANES

BACKGROUND OF THE INVENTION

This invention relates to a new process for the production of urethanes by reacting aromatic amino compounds with alcohols and carbon monoxide in the presence of catalyst systems containing sulfur and/or selenium and/or compounds of these elements. Urethanes have generally been formed by reacting an aromatic isocyanate with an alcohol, the isocyanate in turn having been obtained by reacting phosgene with the corresponding primary amine. The amine was generally produced by reduction of the corresponding nitro compound. Unfortunately, this conventional process is attended by various disadvantages, not the least of which are the toxicity and the corrosive nature of phosgene and the formation of hydrogen chloride as a secondary product.

Accordingly, there have been numerous attempts to bypass the highly toxic phosgene and to produce the urethanes directly from the corresponding nitrogen compounds and the corresponding alcohols in the presence of carbon monoxide. For example, U.S. Pat. Nos. 3,338,956; 3,448,140; 3,454,620; 3,467,694; 3,531,512; 3,993,685; 4,052,420 and 4,052,437 and British Pat. Nos. 1,087,896; 1,080,094; 1,246,217; 1,469,222 or 1,472,243 relate to the synthesis of urethanes using catalyst systems containing noble metals of the platinum group or their compounds. U.S. Pat. Nos. 3,895,054 and 3,956,360 and British Pat. Nos. 1,485,108 and 1,486,399 relate to the synthesis of urethanes using catalyst systems containing selenium or compounds of selenium.

The production of urethanes from amino compounds, the corresponding alcohols and carbon monoxide using selenium as a catalyst is also known in the prior art (Chemistry Letters (1972), pages 373–374, published by the Chemical Society of Japan). In the process described in this literature reference, it is necessary to use stoichiometric quantities of selenium which results in considerable catalyst losses. Despite the use of relatively large quantities of selenium, the yields of urethane are very low when aromatic amines are used as the starting material. Furthermore, selenium and compounds of selenium are toxicologically unacceptable substances. In addition, selenium and its compounds leave the final urethane with an unpleasant odor.

The object of the present invention is to provide an improved process for the production of urethanes from aromatic amino compounds, alcohols and carbon monoxide in which either no selenium and/or selenium compounds are used or in which the quantity of selenium and/or selenium compounds can be considerably reduced.

This object is surprisingly achieved by the process according to the present invention.

BRIEF DESCRIPTION OF THE INVENTION

The present invention relates to a process for the production of urethanes comprising reacting aromatic amino compounds with aliphatic, cycloaliphatic or araliphatic alcohols and carbon monoxide in the presence of:
  (a) selenium, selenium compounds, sulphur and/or sulphur compounds,
  (b) aromatic nitro compounds,
  (c) tertiary organic amines and/or alkali metal salts of weak acids,
  (d) oxidizing agents selected from the group consisting of oxygen and oxidizing inorganic compounds of metals of the 1st, 2nd and 5th to 8th Secondary Groups of the Periodic System of Elements which contain chemically bound oxygen and, optionally,
  (e) ammonia and/or aliphatic, araliphatic, cycloaliphatic or heterocyclic amines containing at least one hydrogen atom bound to an amine nitrogen.

Suitable starting aromatic amino compounds include aminobenzene, 4-aminochlorobenzene, 3,4-dichloroaminobenzene, 1,3-diaminobenzene, o-aminotoluene, m-aminotoluene, p-aminotoluene, 2,4-diaminotoluene, 2,6-diaminotoluene, aminonaphthalenes, aminoanthracenes, aminobiphenylenes and the like. In general, the amino compounds suitable for use in the present invention have a molecular weight of from 93 to 300 and contain from 1 to 3 aromatic nuclei, from 1 to 3 amino groups attached to aromatic nuclei and, optionally, other substituents which are inert under the reaction conditions of the instant process. The preferred amino compounds include aniline, aminobenzene and the above-mentioned diaminotoluenes. Mixtures of the above-mentioned amino compounds may, of course, also be used.

Suitable alcohols include aliphatic, cycloaliphatic or araliphatic alcohols, i.e. preferably any organic compounds otherwise inert under the reaction conditions containing at least one aliphatically, cycloaliphatically or araliphatically bound hydroxyl group and having a molecular weight in the range of from 32 to 300. Examples of suitable alcohols include primary, secondary or tertiary alcohols such as methanol, ethanol, n-propanol, isopropanol, the various isomeric butanols, cyclohexyl alcohol, benzyl alcohol, hexyl alcohol, lauryl alcohol, cetyl alcohol and the like. It is preferred to use monohydric alcohols, particularly ethanol and methanol.

Gaseous carbon monoxide is preferred in the instant process.

The instant process is carried out in the presence of the catalysts and additives mentioned below under (a) to (d) and optionally in the presence of the compounds mentioned under (e). Specifically, these compounds are (a) sulfur and/or selenium and/or compounds of these elements, (b) aromatic nitro compounds, (c) at least one tertiary organic amine and/or at least one alkali metal salt of a weak acid, (d) certain oxidizing agents and, optionally, (e) ammonia and/or at least one aliphatic, araliphatic, cycloaliphatic or heterocyclic amine containing at least one hydrogen atom bound to an amine nitrogen.

Examples of suitable components (a) include elemental sulfur in any form; inorganic or organic compounds, preferably of divalent sulfur other than aromatic thioether compounds such as carbonyl sulfide (COS), hydrogen sulfide, alkali metal sulfides such as sodium sulfide, dimethyl sulfide, diethyl sulfide, thiophene or thiourea. It is preferred to use elemental sulfur, carbonyl sulfide or sulfur compounds which form carbonyl sulfide in situ under the reaction conditions. Other suitable components (a) include selenium in any form, preferably metallic selenium or selenium compounds such as selenium dioxide or carbonyl selenide (COSe). It is also possible, in principle, to use organic selenium compounds such as dimethyl selenide, diphenyl selenide and the like. Elemental selenium is particularly preferred.

Elemental sulfur is the most preferred component (a).

Component (b) may be any organic compound containing aromatically bound nitro groups which, in addition to the said groups, may also contain, in particular, amino groups and urethane groups. In general, component (b) is a compound or mixture of compounds corresponding to the following general formula:

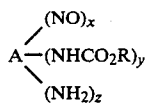

wherein
x represents 1 or 2,
y represents 0 or 1,
z represents 0 or 1,
the sum of x +y +z preferably amounting to 1 or 2, and
A represents a monofunctional, difunctional or trifunctional, preferably monofunctional or difunctional, optionally $C_1$-$C_4$-alkyl-substituted aromatic hydrocarbon radical which preferably corresponds to the aromatic hydrocarbon radical of the aromatic amino compound used in the instant process, and
R represents an aliphatic, cycloaliphatic or araliphatic hydrocarbon radical generally containing up to 18 carbon atoms which preferably corresponds to the hydrocarbon radical of the alcohol component used in the instant process.

Particularly suitable components (b) include nitrobenzene, the isomeric nitrotoluenes, the isomeric dinitrotoluenes, the isomeric aminonitrotoluenes, the isomeric nitro-alkoxy-carbonyl-aminotoluenes and mixtures of these compounds. As already mentioned, it is preferred to use those compounds (b) whose aromatic radical corresponds to the aromatic radical of the aromatic amino compound used in the process. Where aniline is used, nitrobenzene for example is used in accordance with the present invention. Where difunctional amino compounds, for example 2,4-diaminotoluene, are used, the corresponding compounds containing disubstituted toluoyl radicals are also preferably used.

In one, though less preferred, embodiment of the instant process, an aromatic compound containing both a nitro group and an amino group as component (b) is used as the sole reactant for the alcohol and the carbon monoxide because compounds such as these combine the functions of the aromatic amino compounds with those of the aromatic nitro compounds. In this embodiment of the process, compounds such as 2-amino-4'-nitrodiphenyl sulfide, i.e. compounds which contain the above-mentioned groups on different aromatic rings which are not in resonance with one another, are preferred over compounds such as p-nitroaniline, the isomeric nitroanilines or 4-nitro-2-aminotoluene and the isomeric nitro-aminotoluenes.

Component (c) consists of organic bases containing tertiary amino groups, such as tertiary aliphatic amines having a total of from 3 to 20 carbon atoms, for example trimethyl amine, triethyl amine, N,N-dimethyl-octadecyl-amine or trihexyl amine, and heterocyclic tertiary amines such as pyridine or amines containing two tertiary amino groups, such as diazabicyclo-[2,2,2]-octane (triethylene diamine). In addition, bicyclic amidines corresponding to the following general formula:

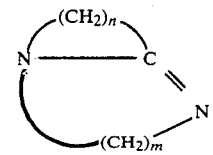

wherein
n represents an integer of from 3 to 5 and
m represents an integer of from 2 to 4
are also suitable.

Basic salts such as alkali metal salts of weak acids, particularly alkali metal carboxylates, such as sodium acetate, potassium acetate, sodium benzoate, or alkali metal salts of weak inorganic acids such as sodium borate or sodium carbonate, may also be used instead of, or in addition to, the above-mentioned tertiary amines as component (c). Preferred components (c) are 1,5-diazabicyclo-[4,3,0]-non-5-ene and 1,8-diazabicyclo-[5,4,0]-undec-7-ene. Another compound preferably used as component (c) is triethylene diamine, particularly in combination with salts corresponding to the following general formula:

MeX wherein
Me represents an alkali metal cation and
X represents an iodide, cyanate or thiocyanate anion.

Potassium acetate and sodium acetate are particularly preferred as component (c).

In cases where combinations are used, the salts just mentioned are generally used in quantities of from 10 to 60 mol % and preferably in quantities of from 5 to 40 mol %, based on the amino compound used.

Suitable oxidizing agents (d) include elemental oxygen or a gas containing oxygen (such as air) and/or oxidizing inorganic compounds of metals containing chemically bound oxygen. These compounds are preferably the corresponding oxides. It is preferred to use the corresponding metal compounds of elements of the 1st, 2nd and 5th to 8th Secondary Groups of the Periodic System. It is particularly preferred, however, to use the corresponding compounds of the elements of the 5th and 6th Secondary Groups and of manganese, iron, cobalt and nickel. Examples of suitable oxidizing agents include iron(II)oxides, iron(III)oxide, mixtures of iron(II) and iron(III)oxides, vanadium(V)oxide, manganese(IV)oxide, molybdenum(VI)oxide, nickel(II) oxide, cobalt(II)oxide, mixtures of the trivalent to hexavalent chromium oxides and mixtures of oxides. Particularly preferred oxidizing agents include iron (III)oxide, mixed oxides containing iron, vanadium and/or molybdenum being especially preferred.

The optionally added component (e) consists of ammonia and/or any aliphatic, araliphatic, cycloaliphatic or heterocyclic amines containing at least one hydrogen atom attached to an amine nitrogen. Component (e) preferably consists of secondary amines corresponding to the following general formula:

$R_1NH-R_2$ wherein
$R_1$ and $R_2$, which may be the same or different, represent $C_1$-$C_6$ alkyl radicals, $C_5$-$C_6$ cycloalkyl radicals, or $R_1$ and $R_2$ together with the secondary amine nitrogen atom form a preferably 6-membered heterocyclic ring optionally containing oxygen as a second hetero-atom.

Preferred amines include dimethyl amine, diethyl amine, dipropyl amine, dibutyl amine, methyl hexyl amine, dihexyl amine or morpholine. Dibutyl amine and morpholine are particularly preferred.

In the practical application of the instant process, the reactants are generally used in such quantities that between 1 and 50, preferably between 5 and 30, hydroxyl groups of the alcohol component are present for each amino group in the aromatic compound used as a starting material. The carbon monoxide is generally used in excess because the reaction is always carried out in a carbon monoxide atmosphere optionally containing the proportion of oxygen according to the present invention.

Where sulfur or a sulfur compound is used, component (a) is used in a quantity corresponding to between 0.1 and 40% by weight, preferably to between 5 and 25% by weight of sulfur in free or bound form, based on the amino compounds used as a starting material. Where selenium or a selenium compound is used, component (a) is used in a quantity corresponding to between 0.01 and 15% by weight, preferably to between 0.1 and 10.0% by weight of free or bound selenium, based on the amino compounds. Component (a) may be first applied to a suitable support such as carbon, aluminum oxide, silicon dioxide, diatomaceous earth, activated clay, zeolite, molecular seives, barium sulfate, calcium carbonate, ion exchange resins and similar materials.

Component (b), which participates in the reaction, is generally present in the reaction mixture in a quantity of from 10 to 70 mol %, preferably in a quantity of from 25 to 60 mol %, based on the total number of mols of the aromatic amines used as a starting compound and component (b).

Component (c) is generally present in the reaction mixture in a quantity of from 5 to 60 mol %, preferably in a quantity of from 5 to 40 mol %, based on the amino compound used as a starting material, these figures applying to the total quantity of basic compounds, but not to the salts corresponding to the formula MeX optionally used.

Where oxygen or an oxygen containing gas is used, component (d), i.e. the oxidizing agent, is used in such a quantity that the proportion of oxygen amounts to between 0.01 and 6.0% by volume, preferably to between 0.1 and 2% by volume, based on the carbon monoxide used. For safety reasons, a proportion of oxygen of 6.0% by volume should not be exceeded. Where oxidizing metal compounds are used, they are generally used in quantities of from 0.1 to 100% by weight, preferably in quantities of from 5 to 40% by weight, based on the amino compound used.

The optionally added component (e) is generally present in the reaction mixture in a quantity of from 0.01 to 20 mol %, preferably in a quantity of from 0.1 to 15 mol %, based on the amino compound used as a starting material.

The instant process may be carried out in the absence of a solvent since the alcohol acts as a solvent, but a separate solvent may also be used. Examples of suitable solvents include aromatic solvents, such as benzene, toluene, xylene, and the like; nitriles such as acetonitrile, benzonitrile and the like; sulfones such as sulfolan. Also suitable as solvents are aliphatic halogenated hydrocarbons such as 1,1,2-trichloro-1,2,2-trifluoroetane, aromatic halogenated hydrocarbons, such as monochlorobenzene, dichlorobenzene, trichlorobenzene, and the like; ketones, esters and other solvents, such as tetrahydrofuran, 1,4-dioxane, 1,2-dimethoxy ethane and the like.

The order in which the starting materials and components (a) to (e) are added is not critical and may be varied as required, depending on the type of apparatus. For example, a starting mixture of alcohol, organic amino compound and components (a) to (e) are introduced into a suitable pressure-resistant reactor, such as an autoclave, after which more carbon monoxide is introduced under pressure, followed by stirring with heating until the urethane-forming reaction is over. Carbon monoxide and, optionally, the oxidizing agent may be introduced into the reactor either semicontinuously or continuously while the carbon dioxide formed as the reaction progresses is separated off. The reaction may be carried out either in batches, semi-continuously or continuously. The carbon monoxide present in excess on completion of the reaction may be re-used by recirculation.

The reaction temperature is generally kept in the range of from 80° to 220° C.; preferably in the range of from 120° to 200° C. Although the reaction takes place more quickly at higher reaction temperatures, the tendency towards thermal decomposition exists at temperatures above 220° C., reducing the yield of urethane product. The reaction pressure, i.e. the initial carbon monoxide pressure prevailing before heating begins, is generally in the range of from 10 to 300 bars, preferably in the range of from 20 to 150 bars. The reaction time is governed by the type of amino compound used, by the reaction temperature and pressure, by the type and quantity of components (a) to (e) and by the type of apparatus used, but generally amounts to between 5 minutes and 6 hours. On completion of the reaction, the reaction mixture is cooled or left to cool. After the gas introduced has been bled off, the reaction mixture is separated, for example by filtration, distillation or by any other suitable method, in order to isolate the urethane formed.

The reaction mixture left after separation of the urethane contains the components (a) to (e) and unseparated urethane residues. It is of advantage to re-use these residues, particularly where the process is carried out continuously.

In the practical application of the process, it is important to work in the absence of water because partial hydrolytic decomposition of the products obtained by the process cannot be precluded in the presence of water.

The important feature of the process according to the invention lies primarily in the simultaneous use of the components (b) and (d) [and, optionally (e)]which, in combination with component (c), enable an excellent conversion to be obtained even when selenium or selenium compounds are used as component (a) in drastically reduced quantities and when sulfur or sulfur compounds are used instead of selenium or selenium compounds. There is no plausible explanation for this surprising effect of the additives of the present invention.

The products obtained by the instant process represent valuable intermediate products for the production of pesticides or for the production of polyurethanes. In particular, the products obtained by the instant process are suitable for use as starting materials for producing the corresponding isocyanates and polyisocyanates by the elimination of the alcohol component by a known method.

The present invention is illustrated but in no way limited by the following Examples. In the Examples, all the reactions were carried out in an autoclave of stainless steel (V4A) provided with a stirrer. The quantities quoted in the Examples were calculated from the results of gas chromatography and liquid chromatography. In selected Examples, the compounds of the instant invention were also isolated.

EXAMPLES

EXAMPLE 1

9.26 g of aniline, 2.45 g of diazabicyclo[2,2,2]-octane, 1.94 g of potassium thiocyanate, 0.14 g of metallic selenium, 8.6 g of nitrobenzene and 140 g of absolute ethanol were introduced into a 0.7 liter autoclave. The autoclave was purged with dry air for five minutes, after which carbon monoxide was introduced under pressure until the initial pressure reached 50 bars at room temperature. The reaction system was heated with stirring to 170° C., followed by stirring for one hour at 170° C. After cooling to room temperature, the reaction solution was relieved of pressure, the autoclave was purged with nitrogen and solid fractions were separated off by filtration. The filtrate obtained was analyzed by gas chromatography. The result was an analysis showing 24.3 g of ethyl-N-phenyl carbamate and 1.5 g of aniline. Gas analysis before the reaction revealed the presence of 0.9% by volume of oxygen and, after the reaction, 0.2% by volume of oxygen in the gas compartment of the reaction vessel.

COMPARISON EXAMPLE

Example 1 was repeated without purging with air, with the proviso that the reaction system was purged with nitrogen before the reaction and then with carbon monoxide. After carbon monoxide had been introduced up to a pressure of 50 bars, the procedure of Example 1 was followed. The filtrate contained only 14.8 g of ethyl-N-phenyl carbamate and 6.1 g of aniline.

EXAMPLE 2

29.9 g of aniline, 0.4 g of selenium, 19.7 g of nitrobenzene, 2 g of potassium acetate, 4 g of a metal oxide mixture of iron(III)oxide and vanadium pentoxide in a ratio by weight of 11:1 and 300 g of absolute methanol were introduced into a 1.3 liter autoclave. The autoclave was purged with nitrogen and then with carbon monoxide. Carbon monoxide was then introduced under pressure into the autoclave until the initial pressure reached 120 bars. The contents of the autoclave were then heated with stirring to 160° C., followed by stirring for two hours at 160° C. According to analysis by gas chromatography, the liquid phase contained 54.8 g of methyl-N-phenyl carbamate and 8.9 g of aniline.

The working up of the mixture of Example 2 to isolate the methyl-N-phenyl carbamate is described as follows:

Solid constituents were filtered off and the solution distilled to remove the methanol. The residue was taken up in 200 g of toluene and the toluene extract was filtered. The toluene was then driven off and the remaining filtrate subjected to distillation. The two distillation fractions were found to be:

(a) first fraction: aniline, 8.4 g $Bp_{0.2}$:65°–70° C.,
(b) second fraction: methyl-N-phenyl carbamate, 54.7 g (97% pure) $Bp_{0.2}$:78°–80° C.

EXAMPLE 3

The procedure as described in Example 2 was repeated using 22.4 g of aniline and 29.6 g of nitrobenzene. An analysis by gas chromatography revealed 65.1 g of methyl-N-phenyl carbamate and 3 g of aniline.

The mixture of Example 3 was worked up in the manner described in Example 2 with extraction of the filtered toluene extract by shaking with aqueous sodium hydroxide (2.5%) and water. The aqueous phase was then separated off, the toluene was removed from the organic phase and the remainder of the organic phase was subjected to distillation. Analysis showed the following compositions:

(a) first fraction: aniline, 2.0 g $Bp_{0.2}$:65°–68° C.,
(b) second fraction: methyl-N-phenyl carbamate, 64.8 g (98% pure) $Bp_{0.2}$:78°–81° C.

EXAMPLE 4

22.4 g of aniline, 0.4 g of selenium, 29.6 g of nitrobenzene, 2 g of potassium acetate and 300 g of absolute ethanol were introduced into a 1.3 liter autoclave. The autoclave was purged with dry air for five minutes, after which carbon monoxide was introduced under pressure until the initial pressure reached 120 bars at room temperature. The contents of the autoclave were heated with stirring to 150° C., followed by stirring for two hours at 150° C. Analysis by gas chromatography revealed the liquid phase to contain 64.4 g of ethyl-N-phenyl carbamate and 4.5 g of aniline.

EXAMPLE 5

33.6 g of aniline, 0.4 g of selenium, 14.8 g of nitrobenzene, 2 g of potassium acetate, 4 g of the metal oxide mixture similar to Example 2 and 300 g of absolute ethanol were introduced into a 1.3 liter autoclave. The reaction was carried out in the manner described in Example 2 (three hours at 150° C.). Analysis by gas chromatography revealed that the liquid phase contained 39.8 g of ethyl-N-phenyl carbamate and 18.7 g of aniline.

EXAMPLE 6

7.5 g of aniline, 0.2 g of selenium, 19.7 g of nitrobenzene, 1 g of potassium acetate, 2 g o2f the metal oxide mixture similar to Example 2 and 150 g of absolute ethanol are reacted for 150 minutes in a 0.7 liter autoclave in the manner described in Example 5. Analysis by gas chromatography revealed 32.6 g of ethyl-N-phenyl carbamate and 2.4 g of aniline.

EXAMPLE 7

22.0 g of 2,4-diaminotoluene, 1.0 g of selenium, 32.7 g of 2,4-dinitrotoluene, 4 g of potassium acetate, 6 g of the metal oxide mixture according to Example 2 and 300 g of absolute methanol were introduced into a 1.3 liter autoclave. The air in the autoclave was replaced by nitrogen gas and then by carbon monoxide. Carbon monoxide was then introduced under pressure into the autoclave until the initial pressure had reached 120 bars at room temperature. The reaction system was heated with stirring and kept for three hours at 160° C. Analysis by liquid chromatography of the reaction mixture separated from the selenium and metal oxide mixture, to which 200 g of methanol were additionally added for reasons of solubility, revealed 67.3 g of 2,4-dimethoxycarbonyl-aminotoluene and 1.0 g of 2,4-diaminotoluene. Slow cooling to -10° C. produced 62,5 g of crystalline 2,4-dimethoxy-carbonyl-aminotoluene melting at from 166 to 168° C.

EXAMPLE 8

11.0 g of 2,4-diaminotoluene, 1.0 g of selenium, 16.4 g of 2,4-dinitrotoluene, 2 g of potassium acetate, 3 g of the metal oxide mixture according to Example 2 and 250 g of absolute ethanol were reacted in the manner described in Example 2. Analysis by liquid chromatography revealed 25.4 g of 2,4-diethoxy-carbonylaminotoluene and 1.3 g of 2,4-diaminotoluene.

EXAMPLE 9

14.7 g of 2,4-diaminotoluene, 1.0 g of selenium, 10.9 g of 2,4-dinitrotoluene, 2 g of potassium acetate, 200 g of absolute methanol and 3 g of the metal oxide mixture according to Example 2 were reacted in a 0.7 liter autoclave in the manner described in Example 2. Analysis revealed 19.5 g of 2,4-dimethoxy-carbonylaminotoluene and 3.3 g of 2,4-diaminotoluene.

EXAMPLE 10

Example 9 was repeated using 250 g of absolute ethanol instead of methanol. Analysis by liquid chromatography revealed 17.9 g of 2,4-diethoxy-carbonylaminotoluene and 2.1 g of 2,4-diaminotoluene.

EXAMPLE 11

15.3 g of 4-chloroaniline, 2 g of sulfur, 18.9 g of 4-nitrochlorobenzene, 1 g of potassium acetate, 2 g of the metal oxide mixture according to Example 2, 0.6 g of di-n-butyl amine and 150 g of ethanol were reacted in a 0.7 liter autoclave in the manner described in Example 2. According to analysis by gas chromatography, the liquid phase contained 24.5 g of ethyl-N-(4-chlorophenyl)-carbamate and 7.8 g of 4-chloroaniline.

EXAMPLE 12

14.9 g of aniline, 0.5 g of selenium, 9.8 g of nitrobenzene, 1 g of 1,8-diazabicyclo-[5,4,0]-undec-7-ene, 3 g of the metal oxide mixture according to Example 2 and 150 g of absolute methanol were reacted for one hour at 170° C. in the manner described in Example 11. Analysis by gas chromatography revealed 19.9 g of methyl-N-phenyl carbamate and 6.5 g of aniline.

EXAMPLE 13

16.8 g of aniline, 0.2 g of selenium, 7.4 g of nitrobenzene, 1 g of potassium acetate, 3 g of the metal oxide mixture according to Example 2 and 150 g of absolute methanol were reacted for three hours at 150° C. in the manner described in Example 11. Analysis by gas chromatography revealed 20.3 g of methyl-N-phenyl carbamate and 5.9 g of aniline.

EXAMPLE 14

14.9 g of aniline, 2 g of sulfur, 9.9 g of nitrobenzene, 1 g of potassium acetate, 0.6 g of di-n-butylamine, 2 g of the metal oxide mixture according to Example 2 and 150 g of absolute methanol were reacted for two hours at 170° C. in the manner described in Example 11. Analysis by gas chromatography revealed 15.8 g of methyl-N-phenyl carbamate and 12.5 g of aniline.

COMPARISON EXAMPLE

Example 14 was repeated without the metal oxide mixture and without di-n-butylamine. Analysis by gas chromatography revealed 1.8 g of methyl-N-phenyl carbamate and 11.6 g of aniline.

EXAMPLE 15

Example 3 was repeated using 1.3 g of di-n-butylamine, 4 g of sulfur instead of selenium and 300 g of absolute ethanol instead of methanol. Analysis by gas chromatography revealed 40.3 g of ethyl-N-phenyl carbamate and 17.6 g of aniline.

EXAMPLE 16

30.4 g of 4-nitro-2-aminotoluene, 0.5 g of selenium, 2 g of potassium acetate, 3 g of the metal oxide mixture according to Example 2 and 200 g of absolute methanol were reacted in a 0.7 liter autoclave in the manner described in Example 2. Analysis by liquid chromatography revealed 39,5 g of 2,4-dimethoxy-carbonyl-amino toluene.

EXAMPLE 17

29,5 g of 2-amino-4'-nitro-diphenyl sulfide, 0,4g of selenium, 2 g of potassium acetate, g of a mixture of metal oxides according to example 2 and 150 g g absolute methanol were reacted for three hours at 150° C. in the manner described in Example 16. Following the separation of insoluble fractions, 25.2 g of 2,4'-dimethoxy-carbonyl-aminodiphenyl sulfide were obtained by crystallization, Mp: 136°–137° C.

What is claimed is:

1. A process for the production of urethanes comprising reacting aromatic amino compounds, optionally having substituents other than amino groups which are inert under the reaction conditions of the instant process with aliphatic, cycloaliphatic or araliphatic alcohols and carbon monoxide in the presence of
   (a) selenium, selenium compounds, sulfur and/or sulfur compounds,
   (b) aromatic nitro compounds,
   (c) tertiary organic amines and/or alkali metal salts of weak acids,
   (d) oxidizing agents selected from the group consisting of oxygen, gases containing oxygen and oxidizing inorganic compounds of metals of the 1st, 2nd and 5th to 8th Secondary Groups of the Periodic System of Elements, said inorganic compounds containing chemically bound oxygen and, optionally,
   (e) ammonia and/or aliphatic, araliphatic, cycloaliphatic or heterocyclic amines containing at least one hydrogen atom attached to an amine nitrogen.

2. A process as claimed in claim 1, wherein said aromatic amino compound is aniline.

3. A process as claimed in claim 1, wherein said aromatic amino compound is diaminotoluene.

4. A process as claimed in claim 1, wherein said alcohol is ethyl alcohol.

5. A process as claimed in claim 1, wherein said alcohol is methyl alcohol.

6. A process as claimed in claim 1, wherein said component (a) is metallic selenium.

7. A process as claimed in claim 1, wherein said component (a) is sulfur.

8. A process as claimed in claim 1, wherein said component (b) is nitrobenzene.

9. A process as claimed in claim 1, wherein said component (b) is dinitrotoluene.

10. A process as claimed in claim 1, wherein said component (c) is a tertiary organic amine and/or an alkali metal salt of a weak acid selected from the group comprising triethylene diamine, potassium acetate and sodium acetate.

11. A process as claimed in claim 1, wherein said component (c) is a tertiary amine and a salt corresponding to the general formula:

$$MeX$$

wherein

Me represents an alkali metal cation, and

X represents an iodide, cyanide or thiocyanate anion.

12. A process as claimed in claim 1, wherein said component (c) is a tertiary amine.

13. A process as claimed in claim 1, wherein said component (c) is a bicyclic amidine of the general formula:

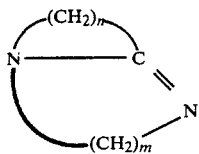

wherein
n represents an integer of from 3 to 5 and
m represents an integer of from 2 to 4.

14. A process as claimed in claim 1, wherein said component (c) is 1,5-diazabicyclo-[4,3,0]-non-5-ene.

15. A process as claimed in claim 1, wherein said component (c) is 1,8-diazabicyclo-[5,4,0]-undec-7-ene.

16. A process as claimed in claim 1, wherein the reaction is carried out at a temperature of from 80° to 220° C. and a pressure of from 10 to 300 bars.

17. A process as claimed in claim 1, wherein the reaction is carried out at a temperature of from 120° to 200° C. and a pressure of from 20 to 150 bars.

18. A process as claimed in claim 1, wherein said component (a) is selenium and/or a selenium compound in a concentration of from 0.01 to 15%, by weight, preferably 0.1 to 10.0%, by weight, of free or bound selenium, based on said amino compounds.

19. A process as claimed in claim 1, wherein said component (a) is sulfur and/or a sulfur compound in a concentration of from 0.1 to 40%, by weight, preferably from 5 to 25%, by weight, of free or bound sulfur, based on said amino compounds.

20. A process as claimed in claim 1, wherein said component (b) is from 10 to 70 mol %, preferably 25 to 60 mol %, based on the total mols of said aromatic amines and said component (b).

21. A process as claimed in claim 1, wherein said component (c) is from 5 to 60 mol %, preferably from 5 to 40 mol %, based on the amount of said amino compound.

22. A process as claimed in claim 1, wherein said component (d) is oxygen or an oxygen containing gas in an oxygen concentration of from 0.01 to 6.0%, by volume, preferably 0.1 to 2.0%, by volume, based on said carbon monoxide used.

23. A process as claimed in claim 1, wherein said component (d) is oxidizing metal compound in a concentration of from 0.1 to 100%, by weight, preferably from 5 to 40%, by weight, based on said amino compound.

24. A process as claimed in claim 1, wherein said optional component (e) is used in a quantity of from 0.01 to 20 mol %, preferably from 0.1 to 15 mol %, based on said amino compound.

* * * * *